United States Patent [19]

Hurst et al.

[11] Patent Number: 5,751,605
[45] Date of Patent: May 12, 1998

[54] MOLECULAR HOLOGRAM QSAR

[75] Inventors: John Robert Hurst, Wildwood; Trevor William Heritage, Ballwin, both of Mo.

[73] Assignee: Tripos, Inc., St. Louis, Mo.

[21] Appl. No.: 698,040

[22] Filed: Aug. 15, 1996

[51] Int. Cl.[6] .................................................. G06F 19/00
[52] U.S. Cl. .............................. 364/496; 364/578
[58] Field of Search .............................. 364/496, 497, 364/498, 499, 578

[56] References Cited

U.S. PATENT DOCUMENTS 5,025,388  6/1991  Cramer, III et al. ................ 364/496

OTHER PUBLICATIONS

Matter et al. "Compound Libraries for Lead Discovery" Chimica Oggi—Chemistry Today v. 14 n. 6 pp. 9–15, (Jun. 1996).

Ormerod et al. "Further Comparative Studies of Fragment Weighting Schemes for Substructural Analysis" Quantitative Structure—Activity Relationships 9(4) pp.302–312, (1990).

*Primary Examiner*—Ellis B. Ramirez
*Assistant Examiner*—M. Kemper
*Attorney, Agent, or Firm*—Laurence A. Weinberger

[57] ABSTRACT

A new computer implemented method for discovering structure-activity relationships has been discovered which utilizes weighted 2D fingerprints in conjunction with the PLS statistical methodology. This method produces a robust QSAR technique that can be automated. In addition, the MOLECULAR HOLOGRAM QSAR technique generates high quality QSAR models that are in many cases as good as or better than models arising from use of more complex and time consuming techniques such as CoMFA or Apex-3D.

1 Claim, No Drawings

MOLECULAR HOLOGRAM QSAR

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Field of Invention

This invention relates to the field of chemical discovery and to understanding the structure/function relationships in biological chemical discovery. In particular, it has been discovered that it is now possible to derive a useful quantitative structure-activity relationship (QSAR) using a weighted 2D fragment molecular metric (MOLECULAR HOLOGRAM) in conjunction with the partial least squares (PLS) method of multivariate analysis.

2. Description of Related Art

1. Computational Chemistry Environment

Generally, all calculations and analyses to derive structure-activity relationships are implemented in a modern computational chemistry environment using software designed to handle molecular structures and associated properties and operations. For purposes of this Application, such an environment is specifically referenced. In particular, the computational environment and capabilities of the *SYBYL* and *UNITY* software programs developed and marketed by Tripos, Inc. (St. Louis, Mo.) are specifically utilized. Unless otherwise noted, all software references and commands in the following text are references to functionalities contained in the *SYBYL* and *UNITY* software programs. All MOLECULAR HOLOGRAMS may be derived using *SYBYL* and *UNITY*. Where a required functionality is not available in *SYBYL* or *UNITY*, the software code to implement that functionality is provided in an Appendix to this Application. Software with similar functionalities to *SYBYL* and *UNITY* are available from other sources, both commercial and non-commercial, well known to those in the art. A general purpose programmable digital computer with ample amounts of memory and hard disk storage is required for the implementation of this invention. In performing the methods of this invention, representations of molecules and/or molecular structures as well as other data may need to be stored simultaneously in the random access memory of the computer or in rapidly available permanent storage. The inventors use a Silicon Graphics, Inc. *Indigo* computer having a single 150 Mhz R4400 processor with 128 Mb memory and 4 Gb hard disk storage space.

2.2D Fingerprints

Molecular fingerprints are primarily used to efficiently search databases and to analyze chemical similarity[1]. Similarity assessments based on 2D fingerprints are most commonly performed using the Tanimoto coefficient[2], which compares the number of fingerprint bits in common between pairs of structures. Most recently, a technique has been developed which identifies structural commonalities in sets of compounds[1]. This technique (known as Stigmata) essentially ANDs (in a Boolean sense) the 2D fingerprints (binary bit strings) of the structures in the data set and identifies fingerprint bits held in common across some percentage of the data set.

There are two general methods of 2D fingerprint generation identified by the companies which develop and promote them. The first, known as the MDL[3] way and second known as the Daylight[4] way. The MDL way requires *a priori* substructural definitions for all the fragments that should be searched for during the fingerprint generation process; if a fragment is not specified in the input list, it will not be included in the fingerprint. The Daylight way uses a set of rules for generating fragments for fingerprinting. The Daylight method uses these rules to generate all possible unbranched fragments. Both methods result in a binary bit string (0s or 1s) that encode the presence or absence of particular fragments.

In the past, attempts to use 2D FINGERPRINTS to generate useful QSARs have not been successful no matter what type of correlation scheme was employed. It is believed that this was the case because an insufficient amount of three-dimensional information about the molecules was contained in the essentially two-dimensional fingerprint.

DEFINITIONS

2D FINGERPRINTS shall mean a 2D molecular measure in which a bit in a data string is set corresponding to the occurrence of a given 2-7 atom fragment in that molecule. Typically, strings of roughly 900 to 2400 bits are used depending on how many different combinations of components are utilized. A particular bit may be set by many different fragments.

MOLECULAR HOLOGRAM shall mean a weighted 2D FINGERPRINT in which all possible fragments are counted with each fragment weighted by the frequency of its occurrence.

DETAILED DESCRIPTION OF THE INVENTION

MOLECULAR HOLOGRAM generation occurs in a fashion analogous to the Daylight method of 2D fingerprint generation except for two critical differences. First, all possible fragments are generated, including the branched and cyclic ones. The second key difference between prior art 2D fingerprints and the MOLECULAR HOLOGRAM is that the MOLECULAR HOLOGRAM actually maintains a count of the number of times each fragment is encountered, and the resulting hologram is a string of integers.

A MOLECULAR HOLOGRAM is defined for a given molecule by generating all possible combinations of fragments with between m and n atoms. The fragments are described using Sybyl Line Notation (SLN), although they could equally well be described using any other connection table format. The fragment SLNs are uniqued and assigned a pseudo-random integer (that is reproducible for a given fragment) and hashed into the range 1 through L, where L represents the length of the MOLECULAR HOLOGRAM. Each time a given fragment is encountered in the molecule, the corresponding hologram bin is incremented.

The hologram length may either be pre-set, in which case non-unique fragments may hash to the same bin (*hashed hologram*), or the hologram length can be calculated on-the-fly to ensure that one and only one type of fragment contributes to each bin (*specific hologram*). Two other types of molecular hologram have been investigated—the *extended hologram* and the *keyed hologram*. The Extended Hologram is used to indicate only the presence of a fragment in the molecule 1 through k times, rather than counting the total number of times each unique fragment occurs. This type of hologram is generated by sub-dividing each bin from the Hashed Hologram into k sub-bins. The Keyed Hologram is based on the Specific Hologram, but counts only fragments which match some sub-structural pattern.

The following features of atoms/molecules can optionally be taken into account during the generation of fragments for hologram construction:

• atomic (elemental) types

• bond types

• atomic connectivity information (equivalent to hybridization of atoms)

• hydrogen atoms may be included or ignored

In the future it may be possible to take the chirality of atoms into account in a way such that the quality of the resulting QSAR is improved. However, at the present time, such a method is not known.

Unlike previous attempts to find useful QSARs by employing conventional 2D FINGERPRINTS, it has been discovered that the application of partial least squares (PLS) or classification analysis to MOLECULAR HOLOGRAMS leads to surprisingly high quality quantitative models relating molecular structure to observed activity (QSAR) across a broad range of activities and molecular structures. The range of activities and molecular structures in the data sets studied included sulfonamide endothelin-A antagonists, anticoccidial triazines, σ1 binding benzyl-N-normetazocines, benzodiazepines, corticosteroids, hydrazide MAO inhibitors, benzindole $5HT_{1a}$ antagonists, and ryanodine analogs. In most cases examined, the methodology of this invention (using the *hashed hologram*) allowed successful derivation of QSAR models comparable or better than those obtained in equivalent studies using traditional molecular descriptors (cLogP/cMR), connectivity indices, or Comparative Molecular Field Analysis (CoMFA).

Advantages of the MOLECULAR HOLOGRAM are that it is simple and rapid to calculate, and it can be readily understood and applied by medicinal chemists to problems of interest. Although the molecular descriptions are derived from 2D information only, the QSAR results are as good as those obtained using the leading 3D QSAR techniques. It is for this reason that these fingerprints are called MOLECULAR HOLOGRAMS since they reflect three-dimensional structures just as a two-dimensional optical hologram contains information about three-dimensional structures. These properties of MOLECULAR HOLOGRAMS render them suitable for application in many areas of pharmaceutical discovery, such as QSAR, database searching and lead prioritization.

As indicated above there are several parameters which control how exactly the MOLECULAR HOLOGRAM is built. The process of QSAR model derivation requires identification of those parameters which lead to an optimal QSAR model. The Sybyl Programming Language (SPL) scripts attached in Appendix "A" have been written to automate this process after initial selected user inputs. The process for using PLS embodied in these SPL scripts is outlined below:

specify atoms, bonds, connections, hydrogens parameters specify how to scale the data for the PLS analysis for each in a series of possible hologram lengths (L)

for each in a series of possible minimum fragment lengths (m)

for each in a series of possible maximum fragment lengths (n)

generate the corresponding molecular hologram apply PLS with leave-one-out cross-validation store parameters used and PLS output loop back to next set of hologram parameters pick the parameter set which yields the best cross-validated model A similar process for using classification analysis is also provided in the SPL scripts. A key component of this process when used with PLS is the internal statistical validation of the models generated using the technique of leave-one-out cross-validation. The method outputs cross-validated $r^2$ values when using PLS and classification success rates when using classification analysis. In each case, the statistical measures are associated with the parameters L, m, and n used to generate the corresponding MOLECULAR HOLOGRAM.

This process determines the optimal (statistically most significant) set of parameters to use in hologram generation such that the resultant hologram yields the optimal validated QSAR model. The SPL script HOLOKEEP of Appendix "A" takes this set of hologram generation parameters as input and regenerates the molecular hologram descriptors, storing them in a SYBYL table. Such a process of validated QSAR model generation has not hitherto been possible, and this process affords huge benefits to the user and extends the scope of QSAR modeling to a much wider audience than is applicable to techniques such as CoMFA or Apex-3D.

This invention using molecular holograms extends far beyond the concept of merely comparing 2D fingerprints in pairwise fashion as is common in the prior art. It has been shown that powerful chemometric techniques, including PLS and discriminant analysis, can be applied to molecular holograms to yield predictive quantitative structure-activity models. Further, the application of the chemometric techniques to the traditional 2D fingerprints described above does not, in general, produce high quality quantitative structure-activity models. No other QSAR method allows parameter adjustment so as to determine the set of parameters to use if generation of an optimal, statistically validated QSAR model is the goal. All other approaches, like CoMFA, force the user to make an arbitrary choice of input parameters and either succeed or fail accordingly. MOLECULAR HOLOGRAM QSAR examines a large set of parameter combinations to find the best set, before it succeeds or fails.

REFERENCES

1. Blankley, C. J. et al, Stigmata: An Algorithm to Determine Structural Commonalities in Diverse Datasets, *J. Chem. Inf. Comput. Sci.* 1996, 34, 862–871

2. Willett, P.; Winterman, V.; Bawden, D. Implementation of Nonhierarchic Cluster Analysis Methods in Chemical Information Systems: Selection of Compounds for Biological Testing and Clustering of Substructure Search Output, *J. Chem. Inf. Comput. Sci.* 1986, 26, 109–118

3. MACCS-II; MDL Ltd.: San Leandro, Calif., 1992

4. James, C. A.; Weininger, D. *Daylight Theory Manual;* Daylight Chemical Information Systems, Inc.: 1995

Details of the SPL Programs

*holograms.spl*—this SPL program cycles through many parameter options, performs crossvalidated PLS analysis with each parameter combination and documents the resulting QSAR models. The output from this program is used to select the optimal set of parameters—i.e. those giving the highest crossvalidated $r^2$ statistic.

*holokeep.spl*—this SPL program takes as input the optimal set of parameters returned by running the *holograms.spl* script. This script then generates a SYBYL table containing the molecular hologram values that can be used for subsequent visualization and computation.

*holosimca.spl*—this SPL program is much the same as the holograms.spl script, except that discriminant analysis is performed instead of PLS. The discriminant analysis code used is the SIMCA code embodied within the release version of SYBYL.

Instructions for Linking and Running the Above SYBYL SPL Programs

The above SPL programs have been written for use with the currently released version of SYBYL (version 6.22). The programs are run as follows:

At the SYBYL command prompt type:

uims load <filename.spl>

Type the programs run name (first word on the line immediately after the header):

holograms (for example)

*Holograms.spl*
*1*

```
@MACRO
###########################################################################

# Application:    HOLOGRAMS (SPL)

# Last Modified: 06-Aug-96

# Copyright:      Tripos Inc.

# Abstract:       SPL script to perform PLS (regression) analysis using hashed hologram descriptor.
#                 Iterates thru' many possible parameter combinations to identify the set yielding the
#                 most differentiating QSAR.

# Author:         Trevor W. Heritage

# Input:          SYBYL table containing Structures and Activity data

# Output:         File containing PLS output for each parameter combination used >> holo.out

# Calls:          %hologram, SYBYL PLS routines

###########################################################################
holograms SybylBasic

setvar sysmsg %system("touch holo.out") >$nulldev
echo "Descriptor Set, Optimal Components, Crossvalidated r2, PRESS value" >>holo.out

# set tailor variables
setvar cgq_save $cgq_timeout
set cgq 0

# read reference table name - must contain only structures and activity data
setvar tbls %system("ls -d *.tbl")
setvar ref %promptif("$1" string "%arg(1 $tbls)" "Enter reference table name" "$tbls")
table recall $ref m100 | >$nulldev
table list brief 1 * |
setvar ref_name %table_default()
setvar nact %table_attribute(ncols)
setvar depend %prompt(int "$nact" "Enter column containing activity data")
setvar nrows %count(%table())

# get user defined parameters for hologram generation
setvar atoms %case("1" "Retain atom type info? " "" "1" "0")
setvar bonds %case("1" "Retain bond type info? " "" "1" "0")
setvar conns %case("1" "Retain connectivity info? " "" "1" "0")
setvar ignoreh %case("1" "Ignore hydrogens? " "" "1" "0")
setvar scale %case("autoscale" "PLS Scaling? " "" "autoscale" "none")

for len in 17 23 29 37 53 97 199 401
  echo "Generating holograms of length: " $len
  for min in 2 3 4 5 6 7
    echo "... min. fragment length: " $min
    for max in 5 6 7 8 9
      echo "...... max. fragment length: " $max
```

Appendix "A" - 2

*Holograms.spl*
*2*

```
        if %gteq($max $min)
                setvar endcol %math($len + $nact)
# create a copy of the reference table
                setvar work_name %cat($ref_name "_" $len "_" $min "_" $max "_" $atoms $bonds $conns
$ignoreh "_" $scale)
                table copy $ref_name $work_name m1 | >$nulldev

# create empty columns for descriptor values
                for cols in %range(1 $len)
                   setvar colhead %cat("H" $cols)
                   table column_append explicit $colhead
                   endfor

# generate hologram and store in current table
                for thisrow in %range(1 $nrows)
                   table mol_show $thisrow | >$nulldev
                   echo "......... processing row number: " $thisrow
                   setvar thisfp %hologram(m1 $len $min $max $atoms $bonds $conns $ignoreh)

# write fingerprint into Sybyl table
                   for thiscol in %range(%math($nact + 1) $endcol)
                        setvar tmp %math($thiscol - $nact)
                        setvar junk %wcell($thisrow $thiscol %arg($tmp $thisfp))
                   endfor
                endfor

# perform QSAR (PLS) analysis on working table
# NB: a maximum of 6 PC's will ever be used for the PLS - this is hard coded
                echo "****** performing PLS analysis ******"
                setvar rows %cat(1: $nrows)
                setvar tmp %math($nact + 1)
                setvar cols %cat($depend "," $tmp ":" $endcol)
                qsar analysis do interactive $rows $cols pls $depend components 6 crossval $nrows scaling
$scale | tmp.pls >$nulldev
                setvar n %math((%math($qsar_optimal_components * 2)) + 8)
                echo $work_name "    " $qsar_optimal_components "    " $qsar_crossvalidated_r_squared "
" %arg($n %qsar_retrieve(standard_errors)) >>holo.out
                echo $qsar_optimal_components "    " $qsar_crossvalidated_r_squared "    " %arg($n
%qsar_retrieve(standard_errors))
                setvar sysmsg %system("rm tmp.pls") >$nulldev

# save and close working table
table save $work_name
                table close $work_name NO

# endif checking if min lteq max
        endif
# end loop over max values
     endfor
# end loop over min values
   endfor
# end loop over len values
endfor
```

Appendix "A" - 3

*Holosimca.spl*

*1*

```
@MACRO
######################################################################

# Application    HOLOSIMCA (SPL)

# Last Modified: 06-Aug-96

# Copyright:     Tripos Inc.

# Abstract:      SPL script to perform SIMCA (classification) analysis using hashed hologram
#                descriptor. Iterates thru' many possible parameter combinations to identify the set
#                yielding the most differentiating QSAR

# Author:        Trevor W. Heritage

# Input:         SYBYL table containing Structures and Activity data

# Output:        File containing SIMCA output for each parameter combination used >> hsimca.out

# Calls:         %hologram, SYBYL SIMCA routines

######################################################################
holosimca SybylBasic
setvar sysmsg %system("touch hsimca.out") >$nulldev

# set tailor variables
setvar cgq_save $cgq_timeout
set cgq 0

# read reference table name - must contain only structures and activity data
setvar tbls %system("ls -d *.tbl")
setvar ref %promptif("$1" string "%arg(1 $tbls)" "Enter reference table name" "$tbls")
table recall $ref m100 | >$nulldev
table list brief 1 * |
setvar ref_name %table_default()
setvar nact %table_attribute(ncols)
setvar depend %prompt(int "$nact" "Enter column containing activity classes")
setvar nrows %count(%table())

# get user defined parameters for hologram generation
setvar atoms %case("1" "Retain atom type info? " "" "1" "0")
setvar bonds %case("1" "Retain bond type info? " "" "1" "0")
setvar conns %case("1" "Retain connectivity info? " "" "1" "0")
setvar ignoreh %case("1" "Ignore hydrogens? " "" "1" "0")

for min in 2 3 4 5 6 7
  echo "... min. fragment length: " $min
  for max in 5 6 7 8 9
    if %gteq($max $min)
        echo "...... max. fragment length: " $max
# generate predefined length hologram
        for len in 50 100
            echo "Generating holograms of length: " $len
            setvar endcol %math($len + $nact)
```

Appendix "A" - 4

*Holosimca.spl*
2

```
# create a copy of the reference table
            setvar work_name %cat($ref_name "_" $len "_" $min "_" $max "_" $atoms $bonds $conns
$ignoreh)
            table copy $ref_name $work_name m1 | >$nulldev

# create empty columns for descriptor values
            for cols in %range(1 $len)
               setvar colhead %cat("H" $cols)
               table column_append explicit $colhead
            endfor

# generate hologram and store in current table
            for thisrow in %range(1 $nrows)
               table mol_show $thisrow | >$nulldev
               echo "......... processing row number: " $thisrow
               setvar thisfp %hologram(m1 $len $min $max $atoms $bonds $conns $ignoreh)
# write fingerprint into Sybyl table
            for thiscol in %range(%math($nact + 1) $endcol)
                  setvar tmp %math($thiscol - $nact)
                  setvar junk %wcell($thisrow $thiscol %arg($tmp $thisfp))
               endfor
            endfor

# perform QSAR (SIMCA) analysis on working table
# NB: a maximum of 6 PC's will ever be used for the analysis - this is hard coded
            echo "****** performing SIMCA analysis ******"
            setvar rows %cat(1: $nrows)
            setvar tmp %math($nact + 1)
            setvar cols %cat($depend "," $tmp ":" $endcol)
            qsar analysis do interactive $rows $cols simca $depend components 6 scaling autoscale |
tmp.simca >$nulldev
            echo "" >>hsimca.out
            echo $work_name >>hsimca.out
            qsar analysis list terminal short_list |
            qsar analysis list terminal short_list | >>hsimca.out
            setvar sysmsg %system("rm tmp.simca") >$nulldev

# write out ASCII version of working table

# save and close working table
table save $work_name
            table close $work_name NO

# end loop over predefined lengths
#           endfor
# endif checking if min lteq max
     endif
# end loop over max values
  endfor
# end loop over min values
endfor
```

Appendix "A" - 5

*Holokeep.spl*
*1*

```
@MACRO
##########################################################################

# Application:    HOLOKEEP (SPL)

# Last Modified: 06-Aug-96

# Copyright:      Tripos Inc.

# Abstract:       SPL script to generate a SYBYL table containing hologram descriptor.  This script
#                 generates the hashed hologram for a particular parameter combination.  The
#                 parameter combination would typically be determined using the SPL program
#                 HOLOGRAMS.SPL

# Author:         Trevor W. Heritage

# Input:          SYBYL table containing Structures

# Output:         SYBYL table containing Structures and Hologram descriptor

# Calls:          %hologram

##########################################################################
holokeep SybylBasic

# read reference table name - must contain only structures and activity data
setvar tbls %system("ls -d *.tbl")
setvar ref %promptif("$1" string "%arg(1 $tbls)" "Enter reference table name" "$tbls")
table recall $ref m100 | >$nulldev
table list brief 1 * |
setvar ref_name %table_default()
setvar nact %table_attribute(ncols)
setvar nrows %count(%table())

# get user defined parameters for hologram generation
setvar atoms %case("1" "Retain atom type info? " "" "1" "0")
setvar bonds %case("1" "Retain bond type info? " "" "1" "0")
setvar conns %case("1" "Retain connectivity info? " "" "1" "0")
setvar ignoreh %case("1" "Ignore hydrogens? " "" "1" "0")
setvar len %prompt(int "50" "Enter length of hologram to generate")
setvar min %case("2" "Minimum fragment length? " "" "2" "3" "4" "5" "6" "7")
setvar max %case("7" "Maximum fragment length? " "" "5" "6" "7" "8" "9")

setvar endcol %math($len + $nact)
if %gteq($max $min)

# create a copy of the reference table
        setvar work_name %cat($ref_name "_" $len "_" $min "_" $max "_" $atoms $bonds $conns
$ignoreh)
        table copy $ref_name $work_name m1 | >$nulldev

# create empty columns for descriptor values
        setvar end $len
        for cols in %range(1 $end)
```

Appendix "A" - 6

*Holokeep.spl*
*2*

```
            setvar colhead %cat("H" $cols)
            table column_append explicit $colhead
          endfor

# generate hologram and store in current table
          for thisrow in %range(1 $nrows)
            table mol_show $thisrow | >$nulldev
            echo ".......... processing row number: " $thisrow
          setvar thisfp %hologram(m1 $len $min $max $atoms $bonds $conns $ignoreh)

# write fingerprint into Sybyl table
          for thiscol in %range(%math($nact + 1) $endcol)
              setvar tmp %math($thiscol - $nact)
              setvar junk %wcell($thisrow $thiscol %arg($tmp $thisfp))
          endfor
        endfor

# save and close working table
table save $work_name
#         table close $work_name

endif
```

Appendix "A" - 7

We claim:

1. A computer-based method of generating an optimal quantitative structure-activity relationship of a series of molecules comprising the steps of:

(a) defining a list of values for L, m, and n;

(b) selecting a first set of values for L, m, and n from the list;

(c) using the selected values of L, m, and n, defining a MOLECULAR HOLOGRAM molecular structural descriptor for each molecule in the series wherein each molecule is associated with an activity value;

(d) correlating the MOLECULAR HOLOGRAM molecular structural descriptor and activity value of each molecule with all the other molecules in said series;

(e) repeating steps (c) and (d) for all values of L, m, and n on the list; and (c) outputting a table of parameters, including the values of L, m, and n, used for MOLECULAR HOLOGRAM generation along with associated measures of statistical validity.

* * * * *